(12) United States Patent
Larson et al.

(10) Patent No.: US 11,065,137 B2
(45) Date of Patent: Jul. 20, 2021

(54) STENT DELIVERY SYSTEMS WITH A REDUCED PROFILE

(71) Applicant: BOSTON SCIENTIFIC SCIMED, INC., Maple Grove, MN (US)

(72) Inventors: Derek Kenneth Larson, Golden Valley, MN (US); Jim Hemerick, Brooklyn Park, MN (US)

(*) Notice: Subject to any disclaimer, the term of this patent is extended or adjusted under 35 U.S.C. 154(b) by 0 days.

(21) Appl. No.: 15/441,811

(22) Filed: Feb. 24, 2017

(65) Prior Publication Data

US 2017/0246017 A1 Aug. 31, 2017

Related U.S. Application Data

(60) Provisional application No. 62/300,355, filed on Feb. 26, 2016.

(51) Int. Cl.
*A61F 2/966* (2013.01)
*A61F 2/962* (2013.01)
(Continued)

(52) U.S. Cl.
CPC .............. *A61F 2/966* (2013.01); *A61F 2/90* (2013.01); *A61F 2/95* (2013.01); *A61F 2/962* (2013.01);
(Continued)

(58) Field of Classification Search
CPC .. A61F 2/966; A61F 2/95; A61F 2/962; A61F 2250/0039; A61F 2002/9517; A61F 2/2427; A61F 2/2436; A61F 2/9522; A61F 2240/001; A61F 2250/0098; A61M 25/0052; A61M 25/0152; A61M 25/0009; A61M 25/0108; A61M 2025/0024; A61M 2025/0175
(Continued)

(56) References Cited

U.S. PATENT DOCUMENTS 3,613,684 A 10/1971 Sheridan
4,665,918 A 5/1987 Garza et al.
(Continued)

FOREIGN PATENT DOCUMENTS

EP 0676936 A1 10/1995
EP 0684022 A2 11/1995
(Continued)

OTHER PUBLICATIONS

International Search Report and Written Opinion dated May 24, 2017 from International Application No. PCT/US2017/019361.
(Continued)

*Primary Examiner* — George J Ulsh
*Assistant Examiner* — Andrew P. Restaino
(74) *Attorney, Agent, or Firm* — Seager, Tufte & Wickhem, LLP

(57) ABSTRACT

Medical devices, medical device systems, and methods for making and using the same are disclosed. An example medical device may include an inner shaft having a stent receiving region. A bumper shaft may be disposed about the inner shaft. A deployment sheath may be slidably disposed about the inner shaft. The deployment sheath may have a body region and a distal stent covering region. The distal stent covering region may have an outer diameter that is smaller than an outer diameter of the body region.

18 Claims, 17 Drawing Sheets

(51) Int. Cl.
- *A61F 2/95* (2013.01)
- *A61F 2/90* (2013.01)
- *A61M 25/00* (2006.01)
- *A61M 25/01* (2006.01)

(52) U.S. Cl.
CPC .... *A61M 25/0009* (2013.01); *A61M 25/0052* (2013.01); *A61M 25/0108* (2013.01); *A61M 25/0152* (2013.01); *A61F 2/9522* (2020.05); *A61F 2240/001* (2013.01); *A61F 2250/0039* (2013.01); *A61F 2250/0098* (2013.01); *A61M 2025/0024* (2013.01); *A61M 2025/0039* (2013.01); *A61M 2025/0175* (2013.01)

(58) Field of Classification Search
USPC .................................................. 623/1.11
See application file for complete search history.

(56) References Cited

U.S. PATENT DOCUMENTS

| | | |
|---|---|---|
| 4,732,152 A | 3/1988 | Wallsten et al. |
| 4,906,232 A | 3/1990 | Reynolds |
| 5,026,377 A | 6/1991 | Burton et al. |
| 5,071,407 A | 12/1991 | Termin et al. |
| 5,158,548 A | 10/1992 | Lau et al. |
| 5,163,905 A | 11/1992 | Don Michael |
| 5,201,757 A | 4/1993 | Heyn et al. |
| 5,221,261 A | 6/1993 | Termin et al. |
| 5,238,004 A | 8/1993 | Sahatjian et al. |
| 5,346,471 A | 9/1994 | Raulerson |
| 5,378,239 A | 1/1995 | Termin et al. |
| 5,433,723 A | 7/1995 | Lindenberg et al. |
| 5,443,907 A | 8/1995 | Slaikeu et al. |
| 5,445,646 A | 8/1995 | Euteneuer et al. |
| 5,496,277 A | 3/1996 | Termin et al. |
| 5,534,007 A | 7/1996 | St. Germain et al. |
| 5,571,135 A | 11/1996 | Fraser et al. |
| 5,662,703 A | 9/1997 | Yurek et al. |
| 5,674,242 A | 10/1997 | Phan et al. |
| 5,690,644 A | 11/1997 | Yurek et al. |
| 5,695,499 A | 12/1997 | Helgerson et al. |
| 5,702,364 A | 12/1997 | Euteneuer et al. |
| 5,707,376 A | 1/1998 | Kavteladze et al. |
| 5,713,860 A | 2/1998 | Kaplan et al. |
| 5,733,267 A | 3/1998 | Del Toro |
| 5,743,874 A * | 4/1998 | Fischell ............ A61F 2/95 604/103.04 |
| 5,755,777 A | 5/1998 | Chuter |
| 5,772,609 A | 6/1998 | Nguyen et al. |
| 5,772,669 A | 6/1998 | Vrba |
| 5,788,707 A | 8/1998 | Del Toro et al. |
| 5,830,181 A | 11/1998 | Thornton |
| 5,833,694 A | 11/1998 | Poncet |
| 5,833,706 A | 11/1998 | St. Germain et al. |
| 5,843,090 A | 12/1998 | Schuetz |
| 5,843,091 A | 12/1998 | Holsinger et al. |
| 5,882,347 A | 3/1999 | Mouris-Laan et al. |
| 5,891,154 A | 4/1999 | Loeffler |
| 5,906,619 A | 5/1999 | Olson et al. |
| 5,954,764 A | 9/1999 | Parodi |
| 5,957,930 A | 9/1999 | Vrba |
| 5,980,483 A | 11/1999 | Dimitri |
| 6,017,577 A | 1/2000 | Hostettler et al. |
| 6,019,778 A | 2/2000 | Wilson et al. |
| 6,033,413 A | 3/2000 | Mikus et al. |
| 6,059,813 A | 5/2000 | Vrba et al. |
| 6,117,140 A | 9/2000 | Munsinger |
| 6,120,522 A | 9/2000 | Vrba et al. |
| 6,123,723 A | 9/2000 | Konya et al. |
| 6,139,510 A | 10/2000 | Palermo |
| 6,139,524 A | 10/2000 | Killion |
| 6,176,849 B1 | 1/2001 | Yang et al. |
| 6,206,888 B1 | 3/2001 | Bicek et al. |
| 6,221,467 B1 | 4/2001 | Nazarova et al. |
| 6,238,410 B1 | 5/2001 | Vrba et al. |
| 6,254,609 B1 | 7/2001 | Vrba et al. |
| 6,287,329 B1 | 9/2001 | Duerig et al. |
| 6,322,586 B1 | 11/2001 | Monroe et al. |
| 6,330,884 B1 | 12/2001 | Kim |
| 6,331,184 B1 | 12/2001 | Abrams |
| 6,342,066 B1 | 1/2002 | Toro et al. |
| 6,355,060 B1 | 3/2002 | Lenker et al. |
| 6,375,676 B1 | 4/2002 | Cox |
| 6,379,365 B1 | 4/2002 | Diaz |
| 6,380,457 B1 | 4/2002 | Yurek et al. |
| 6,391,050 B1 | 5/2002 | Broome |
| 6,398,802 B1 | 6/2002 | Yee |
| 6,425,898 B1 | 7/2002 | Wilson et al. |
| 6,508,803 B1 | 1/2003 | Horikawa et al. |
| 6,514,228 B1 | 2/2003 | Hamilton et al. |
| 6,514,261 B1 | 2/2003 | Randall et al. |
| 6,533,751 B2 * | 3/2003 | Cragg ............. A61M 25/00 604/264 |
| 6,544,278 B1 | 4/2003 | Vrba et al. |
| 6,576,006 B2 | 6/2003 | Limon et al. |
| 6,589,251 B2 | 7/2003 | Yee et al. |
| 6,602,226 B1 | 8/2003 | Smith et al. |
| 6,613,014 B1 | 9/2003 | Chi |
| 6,626,934 B2 | 9/2003 | Blaeser et al. |
| 6,669,716 B1 | 12/2003 | Gilson et al. |
| 6,709,667 B1 | 3/2004 | Lowe et al. |
| 6,726,712 B1 | 4/2004 | Raeder-Devens et al. |
| 6,726,714 B2 | 4/2004 | DiCaprio et al. |
| 6,736,839 B2 | 5/2004 | Cummings |
| 6,743,219 B1 | 6/2004 | Dwyer et al. |
| 6,755,855 B2 | 6/2004 | Yurek et al. |
| 6,773,446 B1 | 8/2004 | Dwyer et al. |
| 6,776,791 B1 | 8/2004 | Stallings et al. |
| 6,802,849 B2 | 10/2004 | Blaeser et al. |
| 6,860,898 B2 | 3/2005 | Stack et al. |
| 6,939,352 B2 | 9/2005 | Buzzard et al. |
| 6,942,682 B2 | 9/2005 | Vrba et al. |
| 6,951,675 B2 | 10/2005 | Chin et al. |
| 6,989,024 B2 | 1/2006 | Hebert et al. |
| 7,001,423 B2 | 2/2006 | Euteneuer et al. |
| 7,387,640 B2 | 6/2008 | Cummings |
| 7,632,296 B2 | 12/2009 | Malewicz |
| 7,740,652 B2 | 6/2010 | Gerdts et al. |
| 7,867,268 B2 * | 1/2011 | Shelso ............. A61F 2/95 623/1.11 |
| 8,128,676 B2 | 3/2012 | Cummings |
| 8,152,818 B2 | 4/2012 | Gunderson |
| 9,084,692 B2 | 7/2015 | Hacker et al. |
| 2001/0034548 A1 | 10/2001 | Vrba et al. |
| 2001/0034549 A1 | 10/2001 | Bartholf et al. |
| 2001/0037141 A1 | 11/2001 | Yee et al. |
| 2002/0052641 A1 | 5/2002 | Monroe et al. |
| 2002/0058951 A1 | 5/2002 | Fiedler |
| 2002/0082550 A1 | 6/2002 | Hamilton et al. |
| 2002/0095203 A1 | 7/2002 | Thompson et al. |
| 2002/0103525 A1 | 8/2002 | Cummings |
| 2002/0165523 A1 | 11/2002 | Chin et al. |
| 2003/0144671 A1 | 7/2003 | Brooks et al. |
| 2003/0163156 A1 | 8/2003 | Hebert et al. |
| 2004/0098083 A1 | 5/2004 | Tran et al. |
| 2004/0148009 A1 | 7/2004 | Buzzard et al. |
| 2004/0215317 A1 | 10/2004 | Cummings |
| 2004/0267348 A1 | 12/2004 | Gunderson et al. |
| 2005/0027345 A1 | 2/2005 | Horan et al. |
| 2005/0060016 A1 * | 3/2005 | Wu ............. A61F 2/95 623/1.11 |
| 2005/0080476 A1 | 4/2005 | Gunderson et al. |
| 2005/0090890 A1 * | 4/2005 | Wu ............. A61F 2/95 623/1.11 |
| 2005/0113804 A1 | 5/2005 | von Lehe et al. |
| 2005/0149159 A1 | 7/2005 | Andreas et al. |
| 2005/0154439 A1 | 7/2005 | Gunderson |
| 2005/0182473 A1 | 8/2005 | Eidenschink et al. |
| 2005/0182475 A1 | 8/2005 | Jen et al. |
| 2005/0192657 A1 | 9/2005 | Colen et al. |
| 2005/0240254 A1 | 10/2005 | Austin |
| 2005/0256562 A1 | 11/2005 | Clerc et al. |
| 2006/0009833 A1 | 1/2006 | Chobotov et al. |

(56) References Cited

U.S. PATENT DOCUMENTS

| | | |
|---|---|---|
| 2006/0030923 A1 | 2/2006 | Gunderson |
| 2006/0041302 A1 | 2/2006 | Malewicz |
| 2006/0074477 A1 | 4/2006 | Berthiaume et al. |
| 2006/0190069 A1 | 8/2006 | Baker-Janis et al. |
| 2006/0229697 A1 | 10/2006 | Gerdts et al. |
| 2006/0292300 A1 | 12/2006 | Tan |
| 2007/0135803 A1 | 6/2007 | Belson |
| 2007/0142894 A1 | 6/2007 | Moore |
| 2007/0191865 A1 | 8/2007 | Pappas |
| 2007/0208350 A1 | 9/2007 | Gunderson |
| 2007/0233222 A1* | 10/2007 | Roeder .................. A61F 2/95 623/1.11 |
| 2007/0282420 A1 | 12/2007 | Gunderson |
| 2008/0188920 A1 | 8/2008 | Moberg et al. |
| 2008/0208320 A1 | 8/2008 | Tan-Malecki et al. |
| 2009/0024133 A1 | 1/2009 | Keady et al. |
| 2009/0036967 A1 | 2/2009 | Cummings |
| 2009/0157162 A1 | 6/2009 | Chow et al. |
| 2009/0192584 A1 | 7/2009 | Gerdts et al. |
| 2010/0137966 A1* | 6/2010 | Magnuson ............... A61F 2/95 623/1.11 |
| 2010/0256727 A1 | 10/2010 | Gerdts et al. |
| 2011/0301685 A1 | 12/2011 | Kao |
| 2012/0123516 A1* | 5/2012 | Gerdts ................. A61F 2/966 623/1.12 |
| 2012/0158120 A1 | 6/2012 | Hacker et al. |
| 2013/0013047 A1 | 1/2013 | Ramos et al. |
| 2014/0128963 A1 | 5/2014 | Quill et al. |

FOREIGN PATENT DOCUMENTS

| | | |
|---|---|---|
| EP | 0775470 A1 | 5/1997 |
| EP | 0633756 B1 | 2/1998 |
| EP | 0820259 B1 | 2/2003 |
| EP | 1385450 B1 | 3/2007 |
| JP | 2003521332 A | 7/2003 |
| JP | 2013528112 A | 7/2013 |
| WO | 9717899 A1 | 5/1997 |
| WO | 9949808 A1 | 10/1999 |
| WO | 0018330 A1 | 4/2000 |
| WO | 0023139 A1 | 4/2000 |
| WO | 0027309 A1 | 5/2000 |
| WO | 0067828 A1 | 11/2000 |
| WO | 0071059 A1 | 11/2000 |
| WO | 0156501 A1 | 8/2001 |
| WO | 0176676 A2 | 10/2001 |
| WO | 02056953 A2 | 7/2002 |
| WO | 2004098692 A1 | 11/2004 |
| WO | 2005020856 A2 | 3/2005 |
| WO | 2005107644 A1 | 11/2005 |
| WO | 2005112824 A1 | 12/2005 |
| WO | 2006036472 A1 | 4/2006 |
| WO | 2007084370 A1 | 7/2007 |
| WO | 2012068389 A1 | 5/2012 |

OTHER PUBLICATIONS

International Search Report and Written Opinion dated May 24, 2017 for International Application No. PCT/US2017/019361.

* cited by examiner

# STENT DELIVERY SYSTEMS WITH A REDUCED PROFILE

CROSS-REFERENCE TO RELATED APPLICATIONS

This application claims priority under 35 U.S.C. § 119(e) to U.S. Provisional Application No. 62/300,355, filed Feb. 26, 2016, the entire disclosure of which is herein incorporated by reference.

TECHNICAL FIELD

The present disclosure pertains to medical devices, and methods for manufacturing medical devices. More particularly, the present disclosure pertains to stent delivery systems with a reduced profile.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device is disclosed. The medical device comprises:

an inner shaft having a stent receiving region;
a bumper shaft disposed about the inner shaft; and
a deployment sheath slidably disposed about the inner shaft, the deployment sheath having a body region and a distal stent covering region, the distal stent covering region having an outer diameter that is smaller than an outer diameter of the body region.

Alternatively or additionally to any of the embodiments above, further comprising a stent disposed along the stent receiving region.

Alternatively or additionally to any of the embodiments above, the bumper shaft has a body section and a distal section with an outer diameter that is smaller than an outer diameter of the body section.

Alternatively or additionally to any of the embodiments above, a first transition is disposed between the body region and the distal stent covering region of the deployment sheath, wherein a second transition is disposed between the body section and the distal section of the bumper shaft, wherein a stent having a stent length is disposed along the inner member, and wherein the first transition and the second transition are separated by a distance when the deployment sheath is extended distally over the stent.

Alternatively or additionally to any of the embodiments above, the distance is at least as long as the stent length.

Alternatively or additionally to any of the embodiments above, the distance is at least 1.25 times the stent length.

Alternatively or additionally to any of the embodiments above, the distance is at least 1.5 times the stent length.

Alternatively or additionally to any of the embodiments above, further comprising a bumper positioned adjacent to the bumper shaft, the bumper having an outer diameter that is greater than an outer diameter of the bumper shaft.

Alternatively or additionally to any of the embodiments above, the distal stent covering region has a length that suitable for spanning a distance between a knee and an ankle of a patient.

Alternatively or additionally to any of the embodiments above, further comprising an outer shaft disposed along at least a portion of the deployment sheath.

Alternatively or additionally to any of the embodiments above, a step transition region is disposed between the body region of the deployment sheath and the distal stent covering region of the deployment sheath.

Alternatively or additionally to any of the embodiments above, an angled transition region is disposed between the body region of the deployment sheath and the distal stent covering region of the deployment sheath.

A method for manufacturing a stent delivery system is disclosed. The method comprises:

disposing a bumper shaft about an inner shaft, the inner shaft having a stent receiving region;
disposing a deployment sheath disposed about the inner shaft, the deployment sheath having a body region, a distal stent covering region, and a first transition between the body region and the distal stent covering region, the distal stent covering region having an outer diameter that is smaller than an outer diameter of the body region;
disposing a stent along the stent receiving region, the stent having a stent length;
wherein the bumper shaft has a body portion, a distal portion, and a second transition between the body portion and the distal portion; and
wherein the first transition is spaced from the second transition by a distance that has a length that is at least as long as the stent length.

Alternatively or additionally to any of the embodiments above, the distance is at least 1.25 times the stent length.

Alternatively or additionally to any of the embodiments above, the distance is at least 1.5 times the stent length.

A medical device system is disclosed. The medical device system comprises:

an inner shaft having a stent receiving region;
a self-expanding stent disposed along the stent receiving region, the stent having a stent length;
a bumper shaft disposed about the inner shaft;
a deployment sheath slidably disposed about the inner shaft, the deployment sheath having a body region, a distal stent covering region, and a first transition between the body region and the distal stent covering region, the distal stent covering region having an outer diameter that is smaller than an outer diameter of the body region;
wherein the bumper shaft has a body portion, a distal portion, and a second transition between the body portion and the distal portion;
wherein the first transition is spaced from the second transition by a distance that has a length that is at least as long as the stent length; and
a handle coupled to the deployment sheath.

Alternatively or additionally to any of the embodiments above, the distance is at least 1.25 times the stent length.

Alternatively or additionally to any of the embodiments above, the distance is at least 1.5 times the stent length.

Alternatively or additionally to any of the embodiments above, further comprising an outer shaft disposed along at least a portion of the deployment sheath.

Alternatively or additionally to any of the embodiments above, the first transition, the second transition, or both include an angled transition.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
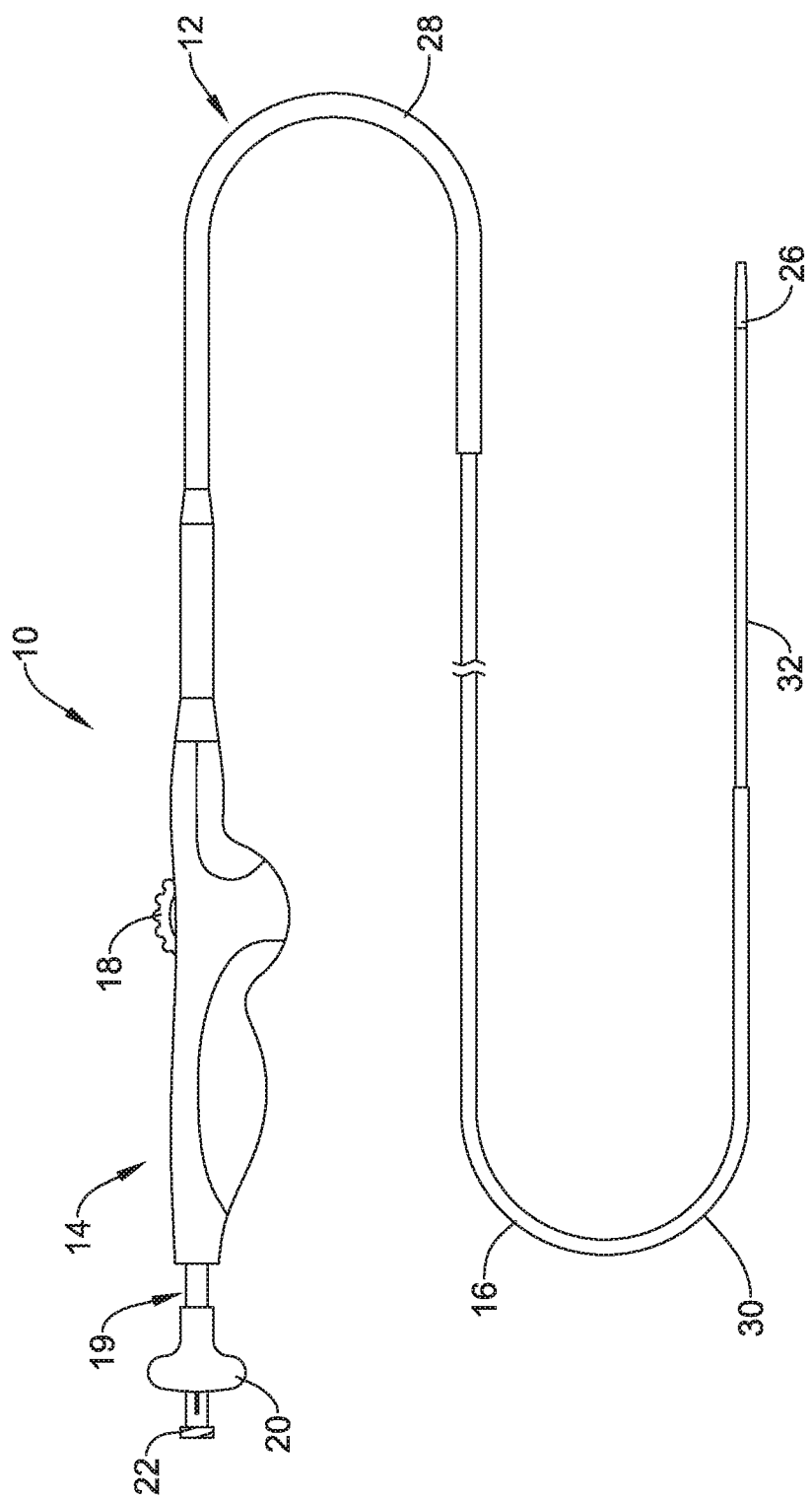
FIG. 1 is a side view of an example medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of mechanical attributes may be important for stent delivery systems (e.g., self-expanding stent delivery systems). Some of these attributions may include trackability, pushability, for transmission (stent deployment force), device profile, etc. It can be appreciated that a change in one of these attributes may impact one or more other attributes. For example, it may be desirable to reduce the profile of a stent delivery system. This may help to minimize the size of the access site and/or allow for access to small anatomical vessels/targets. While reducing the profile, it may be desirable to maintain a desired level of pushability and/or trackability in order to gain access to relatively deep vascular sites. Disclosed herein are stent delivery systems that are designed to provide a desirable balance of mechanical attributes including, for example, profile, pushabilty, and trackability. This may allow the systems disclosed herein to access relatively small anatomical regions including, for example, target vessels "below the knee" or otherwise between the knee and the ankle for delivery and/or deployment of stents. Other targets are contemplated including peripheral vessels, cardiac vessels, carotid arteries, neurological vessels, other vascular locations, or other body lumens.

Figure 3:
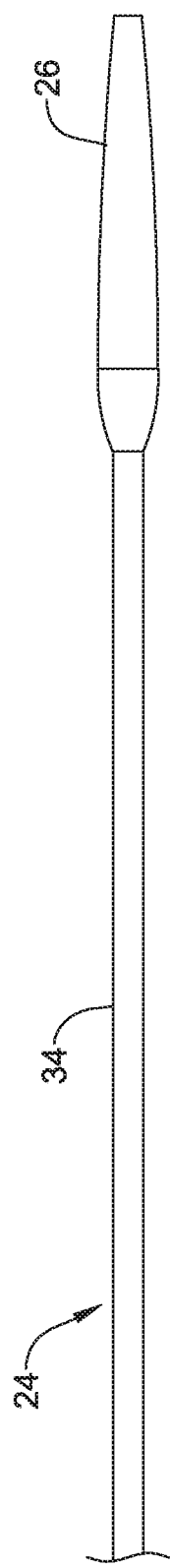
FIG. 3 is a side view of a portion of an example medical device.

FIG. 1 illustrates an example stent delivery system 10. The system 10 may include an elongate shaft 12 and a handle 14 coupled to the shaft 12. In general, the system 10 may be used to deliver a stent, graft, endoprosthesis or the like to an area of interest within a body lumen of a patient. The body lumen may be a blood vessel located near the heart (e.g., within or near a cardiac vessel), within a peripheral vessel, within a neurological vessel, or at any other suitable location. Deployment of the stent may include proximal retraction of a deployment sheath 16, which overlies or otherwise is designed to cover the stent during delivery of the stent. Retraction of the deployment sheath 16 may include the actuation of an actuation member 18 generally disposed at the handle 14. In the example illustrated in FIG. 1, the actuation member 18 is a thumb wheel that can be rotated by a clinician in order to accomplish proximal retraction of the deployment sheath 16. Numerous other actuation members are contemplated. In addition, the shaft 12 may also include an inner shaft or liner (e.g., the inner shaft 24 as illustrated in FIG. 3) terminating in a distal tip 26.

The deployment sheath 16 may be coupled to a rack 19. The rack 19 may include projections or teeth (not shown) that are designed to engage a gear/teeth on or adjacent to actuation member 18. A pull handle 20 and a luer fitting 22 may also be positioned at the proximal end of the rack 19. The pull handle 20 may allow for rapid or course retraction of the deployment sheath 16. The luer fitting 22 may be used to flush various parts of the system 10. The luer fitting 22 may also serve as a guidewire access port.

Figure 2:
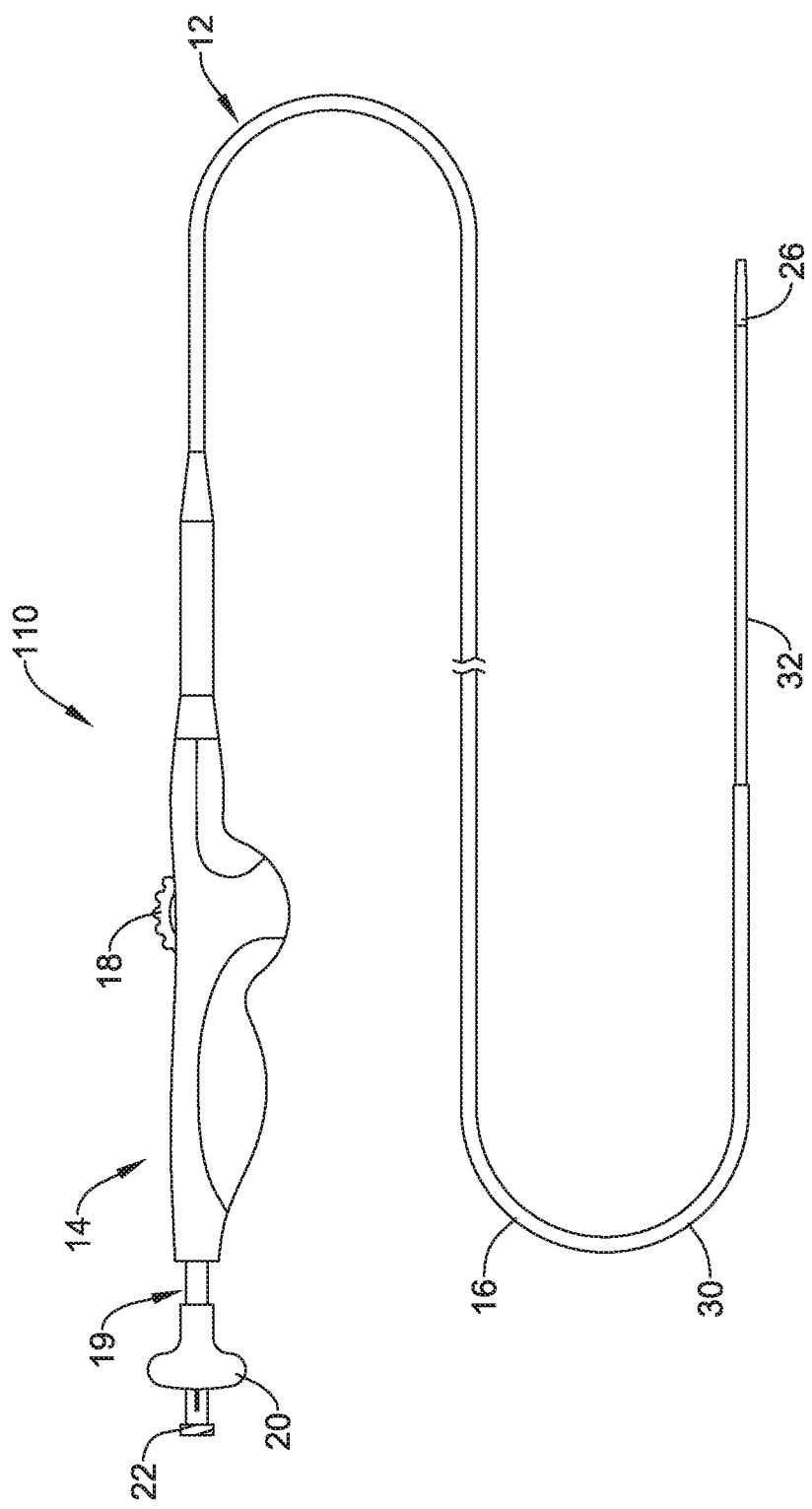
FIG. 2 is a side view of an example medical device.

In some instances, the system 10 may include an outer shaft 28. The outer shaft 28 may help to reduce deployment forces by reducing friction along the deployment sheath 16. To further reduce friction, a lubricant such as a silicone lubricant may be disposed along portions of the deployment sheath 16, the outer shaft 28, and/or other parts of the system 10. As shown in FIG. 2, an example stent delivery system 110 (which may be similar in form and function to other systems disclosed herein) may omit or otherwise lacks the outer shaft 28. For example, the system 10 may be considered to be a "triaxial" system (e.g., including the inner shaft 24, the deployment sheath 16, and the outer shaft 28; also including a bumper shaft 38) whereas the system 110 may be considered to be a "biaxial" or "coaxial" system (e.g., including the inner shaft 24 and the deployment sheath 16; also including the bumper shaft 38).

As indicated above, it may be desirable for the system 10 and/or the system 110 to have a reduced profile. In some instances, the deployment sheath 16 may include a body region 30 and a distal stent covering region 32. The distal stent covering region 32 may have a reduced outer diameter as compared to the body region 30. For example, the body region 30 may have an outer diameter of about 4-8 French (1.333-2.667 mm; 0.053-0.105 inches), or about 5-6 French (1.667-2 mm; 0.066-0.079 inches), or about 5.5 French (1.833 mm; 0.072 inches). The distal stent covering region 32 may have an outer diameter of about 4-8 French (1.333-2.667 mm; 0.053-0.105 inches), or about 4-6 French (1.333-2 mm; 0.053-0.079 inches), or about 5 French (1.667; 0.066 inches). The body region 30 may have a length of about 30-70 inches, or about 35-55 inches, or about 41.3 inches. The distal stent covering region 32 may have a length on the order of about 10-30 inches (25.4-76.2 cm) or about 15-20 inches (38.1-50.8 cm), or about 17.7 inches (45 cm). In at least some instances, the length of the distal stent covering region 32 may approximate the distance between a knee and an ankle in a patient in order to be suitable for accessing vascular locations between the knee and the ankle. Although dimensional ranges are provided herein, other dimensions are contemplated.

In some instances, the distal stent covering region 32 may be formed by reducing the wall thickness of the deployment sheath 16. In such instances, the inner diameter of the deployment sheath 16 may remain substantially constant. Alternatively, the wall thickness of the deployment sheath 16 may remain substantially constant. In such instances, the inner diameter of the body region 30 may be greater than the inner diameter of the distal stent covering region 32. Other instances are contemplated where both the wall thickness and the inner diameter of the body region 30 and/or the distal stent covering region 32 may vary.

The system 10 (and/or the system 110) may include an inner member 24 as illustrated in FIG. 3. In at least some embodiments, the inner member 24 may be a tubular structure and, thus, may include a lumen (not shown). The lumen may be a guidewire lumen that extends along at least a portion of the length of the inner member 24. Accordingly, the system 10 (and/or the system 110) may be advanced over a guidewire to the desired target location in the vasculature. In at least some instances, the inner shaft 24 and/or the lumen extending therethrough may be sized to accommodate a suitable guidewire. For example, the inner shaft 24 may have an inner diameter suitable for accommodating a 0.014 inches guidewire, a 0.018 inches guidewire, a 0.035 inches guidewire, or other suitable sizes. As such, the inner shaft 24 may have an inner diameter of about 0.010-0.050 inches, about 0.012-0.025 inches, about 0.020 inches, or other corresponding sizes. In addition, or in alternative embodiments, the lumen may be a perfusion/aspiration lumen that allows portions, components, or all of the system 10 (and/or the system 110) to be flushed, perfused, aspirated, or the like.

The inner shaft 24 may include a reinforcement (not shown) such as a braid, coil, or the like. In some instances, the reinforcement may extend along the entire length of the inner shaft 24. In other instances, the reinforcement may extend along one or more discrete portions of the inner shaft 24.

The inner member 24 may include a stent receiving region 34 about which a stent (e.g., the stent 36, FIG. 4) may be disposed. The length and/or configuration of the stent receiving region 34 may vary. For example, the stent receiving region 34 may have a length sufficient for the stent to be disposed thereon. It can be appreciated that as the length of the stent utilized for the system 10 (and/or the system 110) increases, the length of the stent receiving region 34 also increases.

Along or otherwise disposed adjacent the stent receiving region 34 may be one or more perfusion ports (not shown). The perfusion ports may extend through the wall of the inner member 24 such that fluid may be infused through the lumen of the inner member 24 and may be flushed through ports. This may be desirable for a number of reasons. For example, the ports may allow a clinician to evacuate air bubbles that may be trapped adjacent the stent by perfusing fluid therethrough. In addition, the ports may be used to aspirate fluid that may be disposed along the inner member 24. The ports may also aid in sterilization and/or other preparatory processing steps that may be involved in preparing the system 10 (and/or the system 110) for sale.

The distal tip 26 may be attached to or otherwise disposed at the distal end of the inner member 24. The distal tip 26 may generally have a rounded or smooth shape that provides a generally atraumatic distal end to system 10. The distal tip 26 may also include one or more cutouts or flats (not shown) formed therein. For the purposes of this disclosure, the flats may be understood to be cutouts or flattened portions of the distal tip 26 where the outer dimension or profile of the distal tip 26 is reduced. The name "flats" comes from the fact that these regions may have a somewhat "flat" appearance when compared to the remainder of the distal tip 26, which generally may have a rounded profile. The shape, however, of the flats is not meant to be limited to being flat or planar as numerous shapes are contemplated. The flats may allow for a gap or space to be defined between the inner member 24 and the deployment sheath 16 when the deployment sheath 16 abuts or otherwise comes into contact with the distal tip 26.

Figure 4:
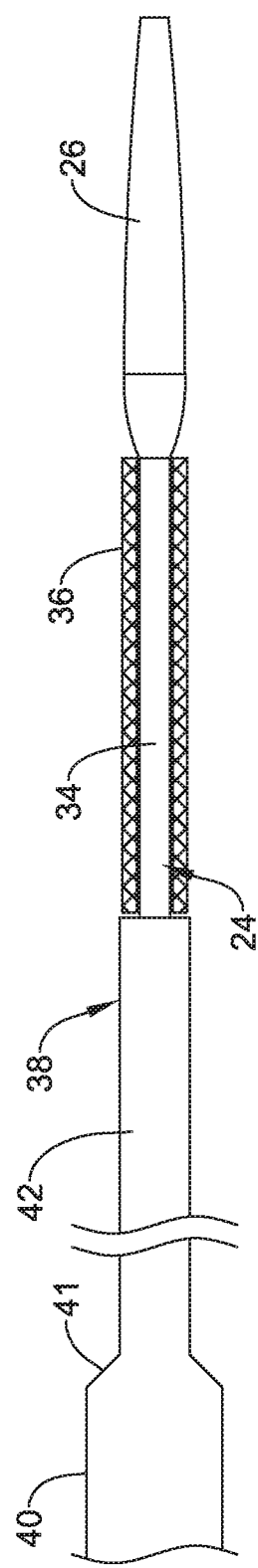
FIG. 4 is a side view of a portion of an example medical device.

FIG. 4 illustrates the inner member 24 with some additional structure of system 10 (and/or the system 110). As shown in FIG. 4, a stent 36 is disposed about the inner member 24 (e.g., about the stent receiving region 34 of the inner member 24). In some embodiments, the stent 36 is a self-expanding stent. Accordingly, the stent 36 may be biased to outwardly expand. Because of this, the stent 36 may not be "loaded onto" the inner member 24 in a strict sense but rather may be thought of as being disposed about or surrounding the inner member 24. The stent 36 may then be restrained within the deployment sheath 16. In alternative embodiments, however, the stent 36 may be directly loaded onto the inner member 24 via crimping or any other suitable mechanical holding mechanism.

A bumper shaft 38 may also be disposed over the inner member 24. In at least some embodiments, the bumper shaft 38 may extend from a position adjacent to the proximal end of the inner member 24 to a position proximal of the distal end of the inner member 24. The bumper shaft 38 may include or otherwise function as a bumper and, thus, may reduce and/or prevent any unwanted proximal movement of the stent 36 during navigation and/or deployment of the stent 36. The bumper shaft 38 may include a reinforcement (not shown) such as a braid, coil, or the like. In some instances, the reinforcement may extend along the entire length of the bumper shaft 38. In other instances, the reinforcement may extend along one or more discrete portions of the bumper shaft 38.

Similar to the deployment sheath 16, the bumper shaft 38 may include a body section 40 and a distal section 42. The distal section 42 may have an outer diameter that is reduced relative to the outer diameter of the body section 40. A first transition 41 may be positioned between the sections 40/42. In some instances, the first transition 41 may take the form of an angled transition or taper as shown in FIG. 4. In other instances, the first transition 41 may be a stepped transition (e.g., a 90 degree step down from the body section 40 to the distal section 42). Other transitions are contemplated. Distal section 42 may be formed by reducing the wall thickness of bumper shaft 38. In such instances, the inner diameter of bumper shaft 38 may remain substantially constant. Alternatively, the wall thickness of bumper shaft 38 may remain substantially constant. In such instances, the inner diameter of body section 40 may be greater than the inner diameter of distal section 42.

Figure 5:
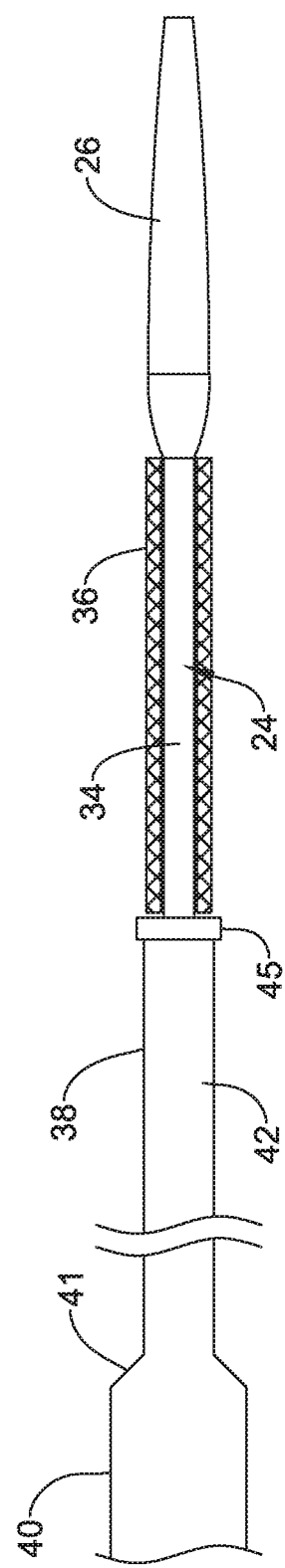
FIG. 5 is a side view of a portion of an example medical device.

In some instances, rather than the bumper shaft 38 functioning as a bumper, a separate bumper 45 may be coupled to the bumper shaft 38 and/or the inner member 24 as shown in FIG. 5. The bumper 45 may help to reduce proximal migration of the stent 36, for example during stent deployment.

Figure 6:
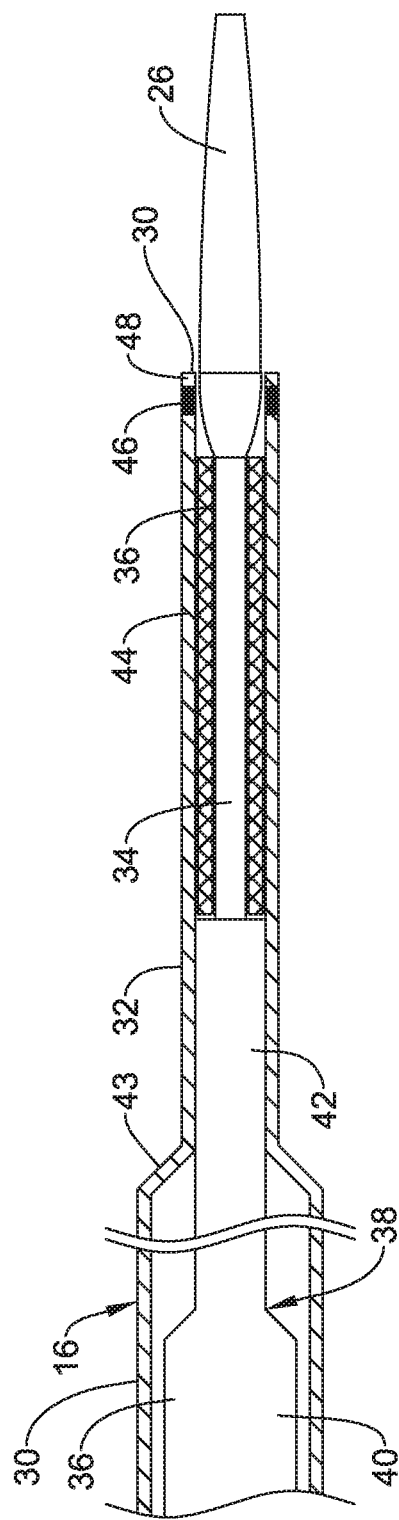
FIG. 6 is a partial cross-sectional side view of a portion of an example medical device.

FIG. 6 illustrates additional structure of the system 10 (and/or the system 110). The deployment sheath 16 is disposed over the inner member 24, the bumper shaft 38, and the stent 36. The deployment sheath 16 is configured to shift between a first position, for example as shown in FIG. 6, such that the deployment sheath 16 is disposed over the stent 36 and a second position where the deployment sheath 16 is proximally retracted to a position substantially proximal of the stent 36. In general, the first position may be utilized during navigation of the system 10 (and/or the system 110) to the appropriate location within a body lumen and the second position may be used to deploy the stent 36.

In at least some embodiments, the deployment sheath 16 may include a second transition region 43 between the portions 30 and 32. The deployment sheath 16 may also include a reinforcing member 44 embedded or otherwise included therewith. The reinforcing member 44 may have any number of different configurations. For example, the reinforcing member 44 may include a braid, a coil, a mesh, combinations thereof, or the like, or any other suitable configuration. In some embodiments, the reinforcing member 44 may extend along the entire length of the deployment sheath 16. In other embodiments, the reinforcing member 44 may extend along one or more portions of the length of the deployment sheath 16. The deployment sheath 16 may also include a radiopaque marker 46. In general, the radiopaque marker 46 may be disposed adjacent to a distal end 48 of the deployment sheath 16. One or more additional radiopaque markers 46 may be disposed along other portions of the deployment sheath 16 or other portions of the system 10 (and/or the system 110). The marker band 46 may allow the distal end 48 of the deployment sheath 16 to be fluoroscopically visualized during advancement of the system 10 (and/or the system 110) and/or deployment of the stent 36. The deployment sheath 16 may also include an inner layer or liner including polytetrafluoroethylene (PTFE) or another suitable material.

Figure 7:
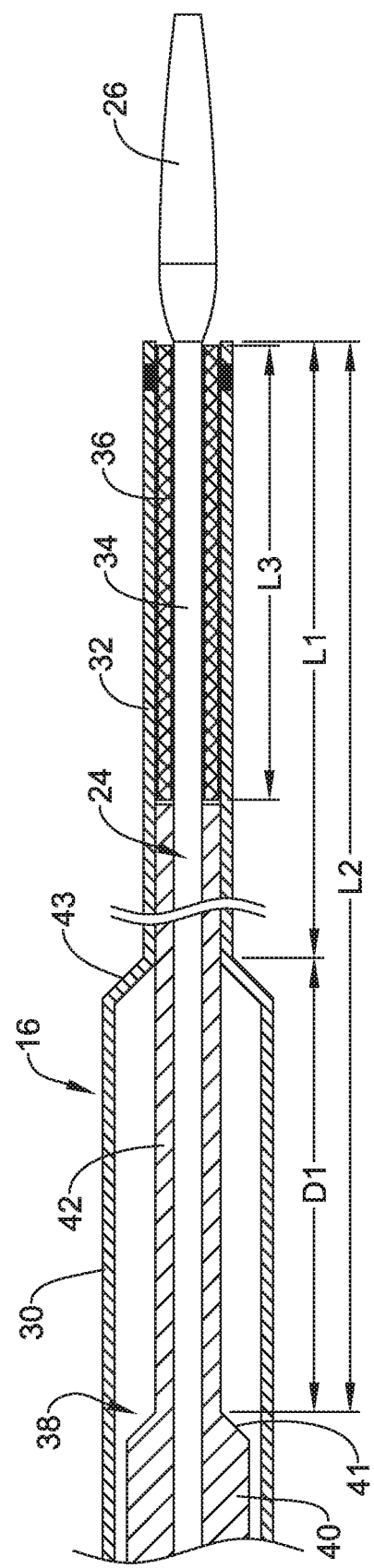
FIG. 7 is a partial cross-sectional side view of a portion of an example medical device.

As shown in FIG. 7, the distal stent covering region 32 has a first length L1. The distal section 42 of the bumper shaft 38 has a second length L2. The stent 36 has a third length L3. The second transition 43 is separated from the first transition 41 by a distance D1. The distance D1 may be greater than or equal to the length of the stent L3 (e.g., when deployment sheath 16 is extended distally over stent 36). This allows the deployment sheath 16 to be retracted and the stent 36 to be deployed before the second transition 43 contacts the first transition 41. In other words, in order for the stent 36 to deployed, the deployment sheath 16 will be proximally retracted to a position where the distal end of the deployment sheath 16 is disposed proximal of the proximal end of the stent 36. Because the distal stent covering region 32 may have an inner diameter that is smaller than an outer diameter of the bumper shaft 38, the distance that the deployment sheath 16 can be proximally retracted may be limited by distance D1. Thus, in order for the deployment sheath 16 to be proximally retracted and deploy the stent 36, the distance D1 is greater than or equal to the length of the stent L3. In some instances, the distance D1 may be at least as long as the length of the stent L3, or about 1-5 times L3, or about 1-3 times L3, or about 1-2 times L3, or about 1.25-1.5 times L3. In at least some instances, the distance D1 may be on the order of about 1-30 cm, or about 5-20 cm, or about 10-15 cm, or about 15 cm.

Figure 8:
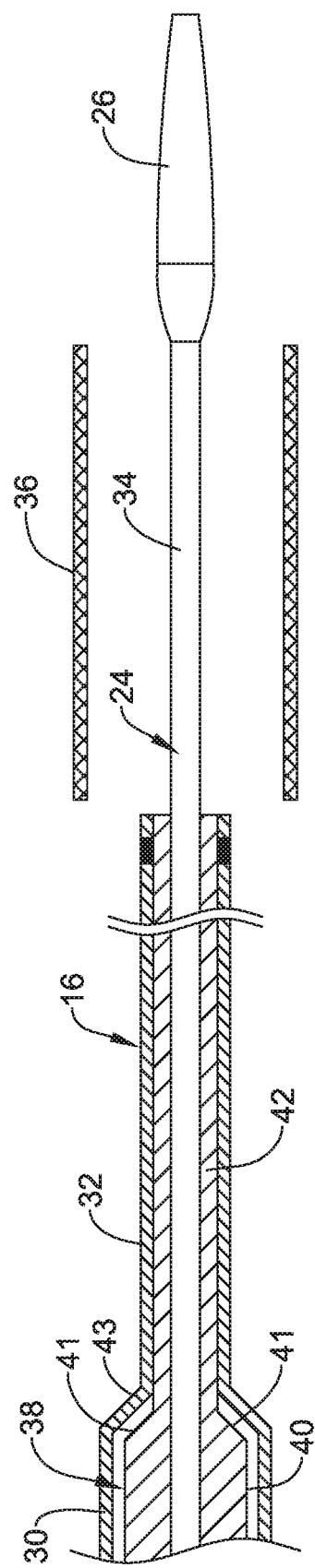
FIG. 8 is a partial cross-sectional side view of a portion of an example medical device.

FIG. 8 illustrates the deployment sheath 16 proximally retracted in order to deploy stent 36. For example, the deployment sheath 16 may be proximally retracted to a position where the first transition 41 is positioned adjacent to the second transition 41. When this happens, the stent 36, which may be self-expanding, can expand, for example, within a target region. It should be noted that if the distance D1 is equal to or approximately equal to the length of the stent L3, the first transition 41 and the second transition 43 may be in contact with one another. In instances where the distance D1 is larger than the length of the stent L3, the first transition 41 and the second transition 43 may be separated spaced apart axially.

Figure 9:
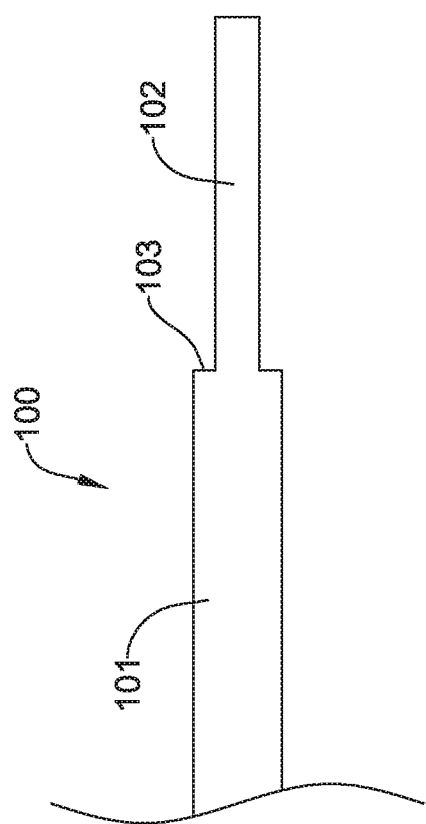
FIG. 9 is a side view of a portion of an example medical device.
Figure 10:
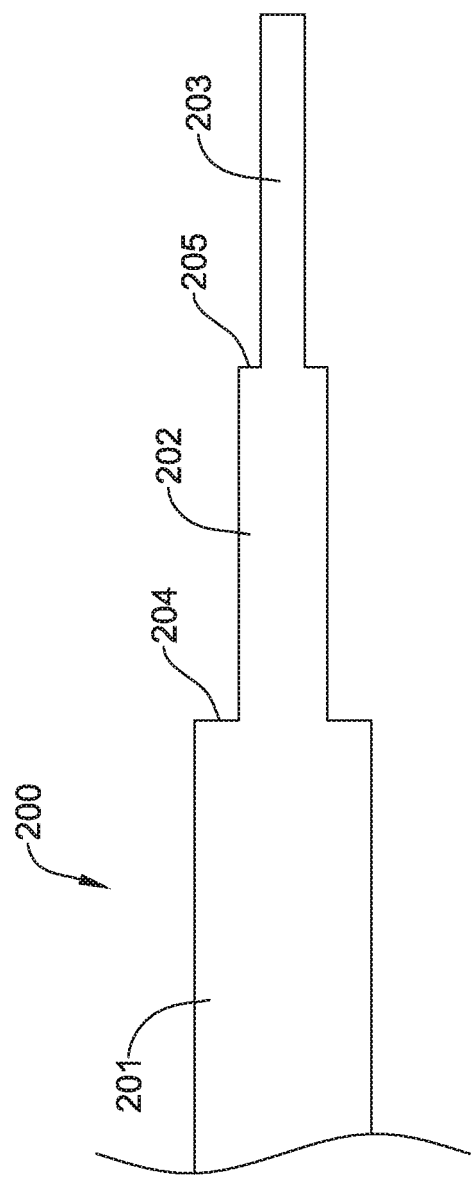
FIG. 10 is a side view of a portion of an example medical device.
Figure 11:
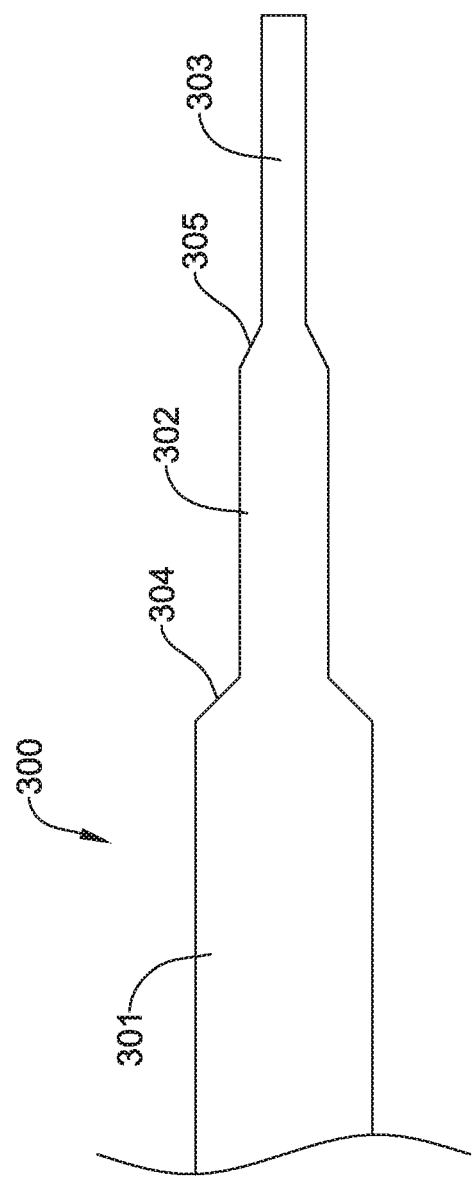
FIG. 11 is a side view of a portion of an example medical device.
Figure 12:
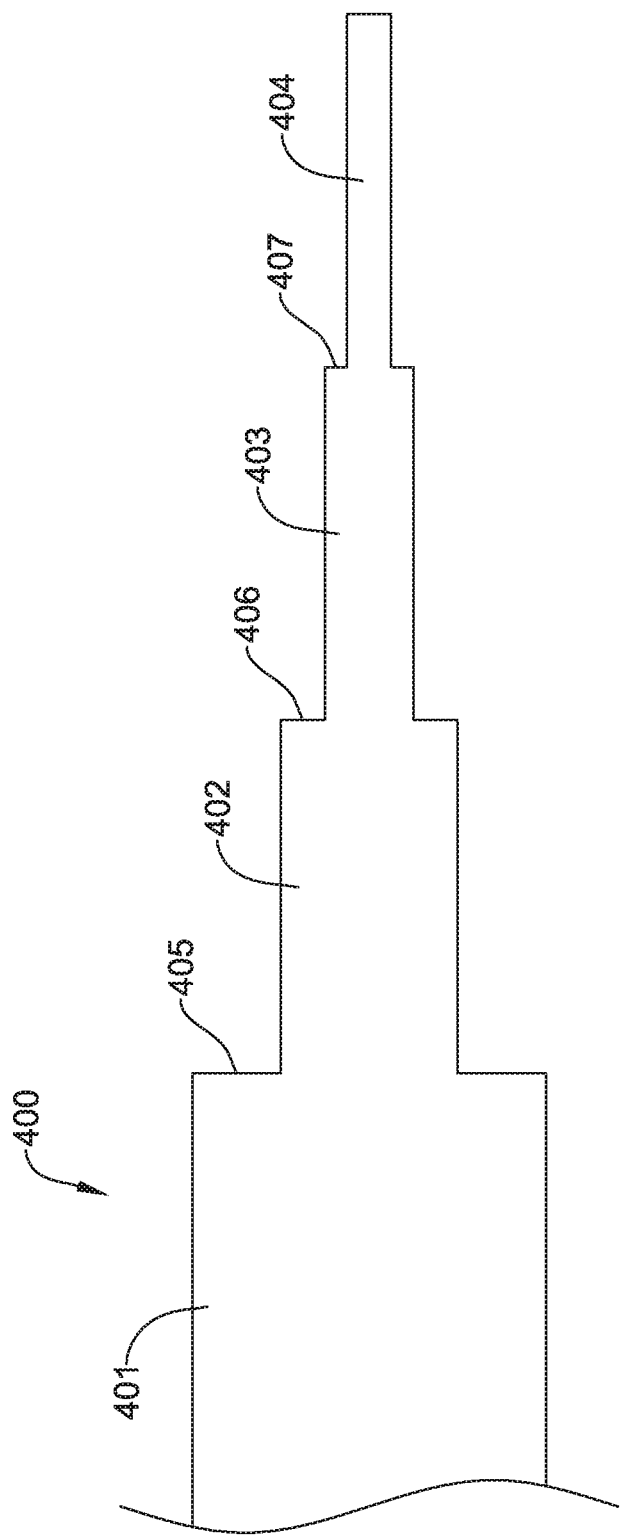
FIG. 12 is a side view of a portion of an example medical device.
Figure 13:
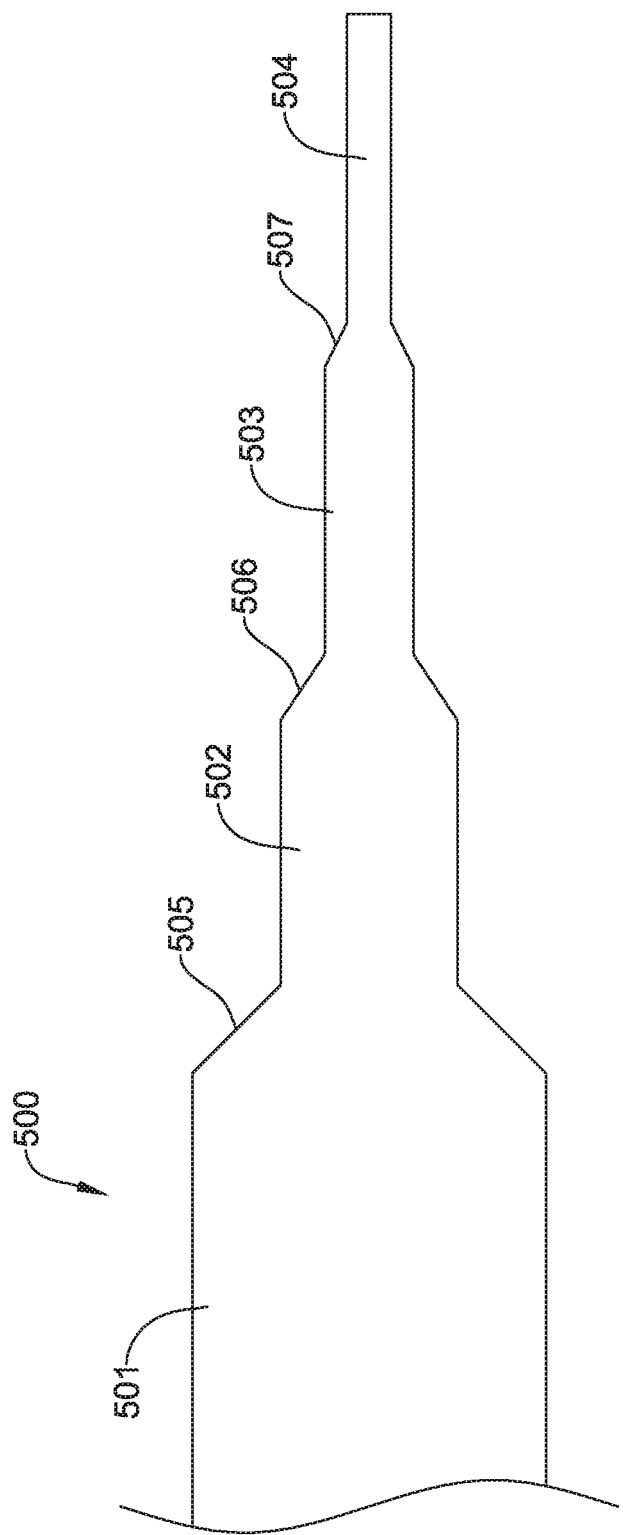
FIG. 13 is a side view of a portion of an example medical device.

FIGS. 9-13 illustrate other contemplated tubular members (e.g., deployment sheaths 16 and/or bumper shafts 38). For the purposes of this disclosure, FIGS. 9-13 may be understood as examples of other configurations that may be utilized for the deployment sheath 16 and/or the bumper shaft 38. For example, FIG. 9 illustrates a tubular member 100 having a first section 101, a second section 102, and a step transition 103 between the sections 101 and 102. Thus, tubular members are contemplated that generally include two sections separated by a stepped transition. FIG. 10 illustrates a tubular member 200 having a first section 201, a second section 202, and a third section 203. A step transition 204 may be positioned between the sections 201 and 202. The step transition 205 may be positioned between the sections 202 and 203. Thus, tubular members are contemplated that generally include at least three distinct sections separated by stepped transitions. That is, tubular members are contemplated that generally include multiple section and multiple stepped transition in alternating configurations, such that each section is distinguishable from an adjacent section by at least one stepped transition. FIG. 11 illustrates a tubular member 300 having a first section 301, a second section 302, and a third section 303. An angled transition 304 may be positioned between the sections 301 and 302. The angled transition 305 may be positioned between the sections 302 and 303. Thus, tubular members are contemplated that generally include three sections separated by angled transitions. FIG. 12 illustrates a tubular member 400 having a first section 401, a second section 402, a third section 403, and a fourth section 404. A step transition 405 may be positioned between the sections 401 and 402. The step transition 406 may be positioned between the sections 402 and 403. The step transition 407 may be positioned between the sections 403 and 404. Thus, tubular members are contemplated that generally include four sections separated by stepped transitions. FIG. 13 illustrates a tubular member 500 having a first section 501, a second section 502, a third section 503, and a fourth section 504. An angled transition 505 may be positioned between the sections 501 and 502. The angled transition 506 may be positioned between the sections 502 and 503. The angled transition 507 may be positioned between the sections 503 and 504. Thus, tubular members are contemplated that include four sections separated by angled transitions. That is, tubular members are contemplated that generally include multiple sections and multiple angled transitions in an alternating configuration, such that each section is distinguishable from an adjacent section by at least one angled transition. Particularly, other tubular members are contemplated that include a suitable number (e.g., 1, 2, 3, 4, or more) of transitions and/or that utilize stepped transitions, angled transitions, or both.

Figure 14:
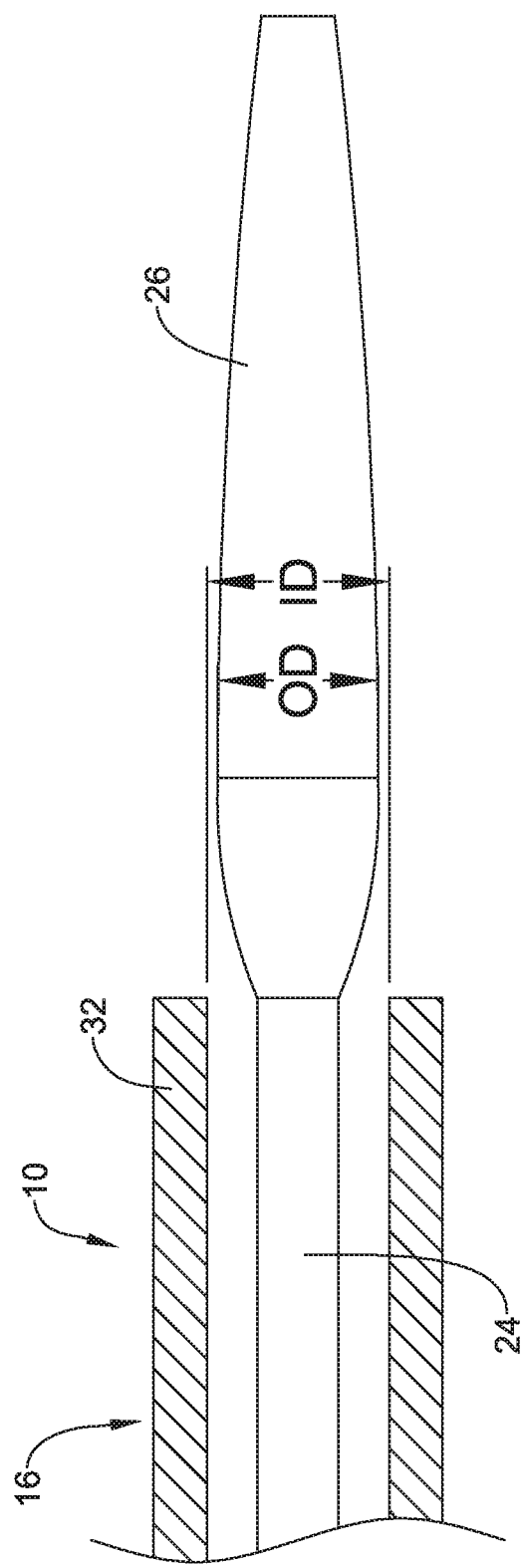
FIG. 14 is a partial cross-sectional side view of a portion of an example medical device.
Figure 15:
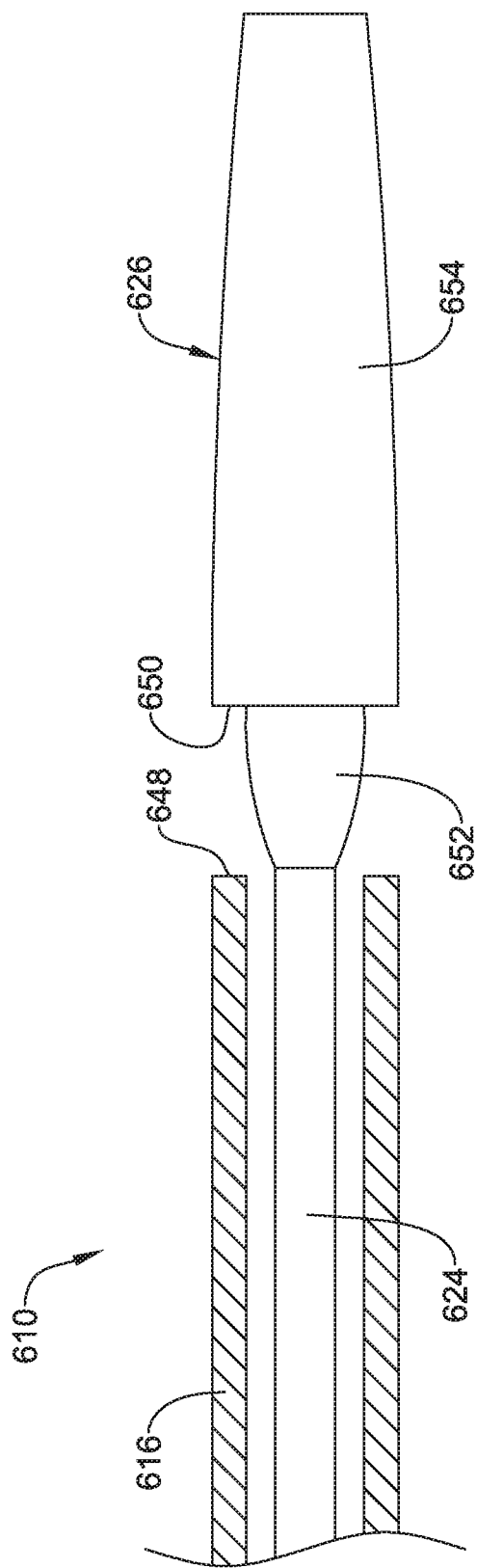
FIG. 15 is a partial cross-sectional side view of a portion of an example medical device.
Figure 16:
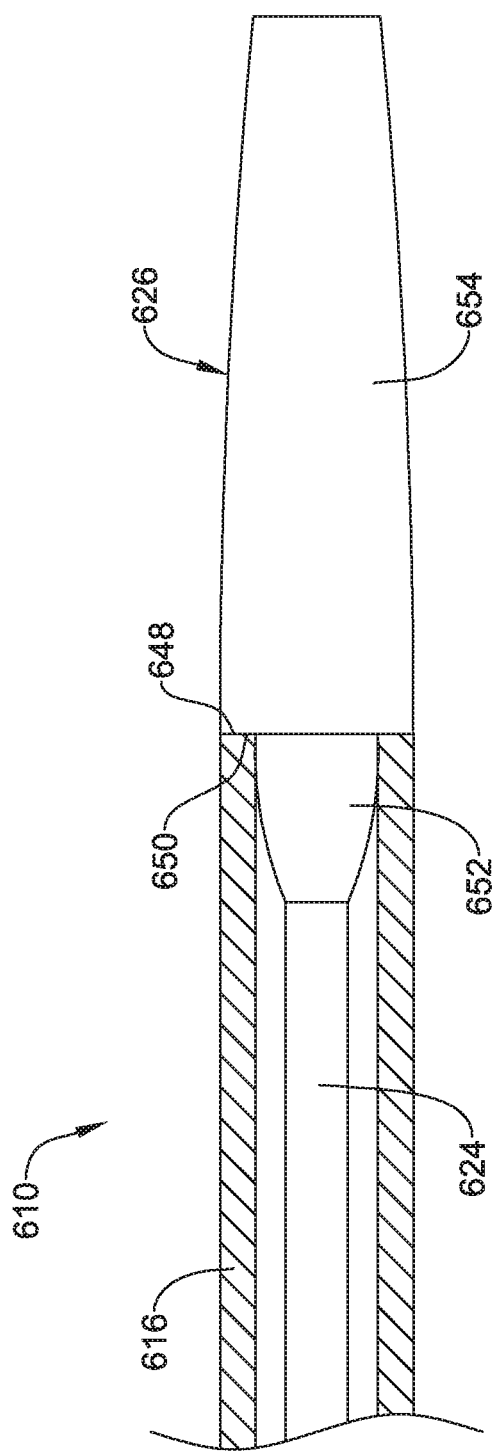
FIG. 16 is a partial cross-sectional side view of a portion of an example medical device.
Figure 17:
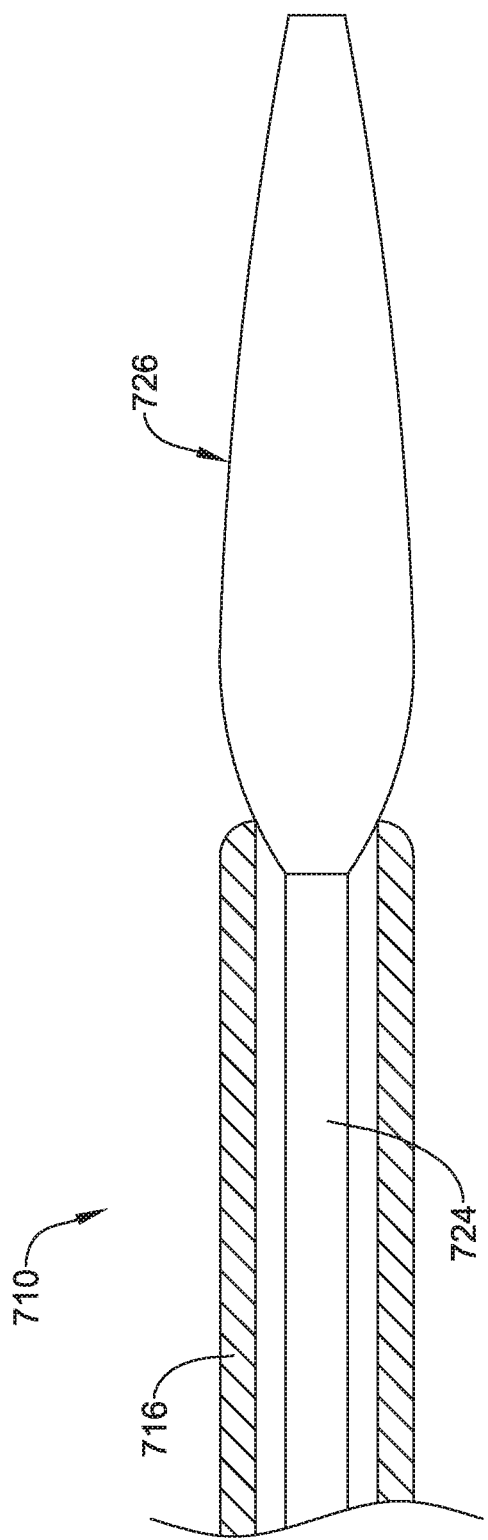
FIG. 17 is a partial cross-sectional side view of a portion of an example medical device.

FIGS. 14-17 illustrate some of the contemplated tip configurations. For example, FIG. 14 illustrates the system 10 including a distal tip 26 having an outer diameter OD that is less than or equal to an inner diameter ID of the distal stent covering region 32 of the deployment sheath 16. FIG. 15 illustrates a system 610, which may be similar in form and function to other systems disclosed herein, where the inner member 624 includes a distal tip 626. The distal tip 626 has a proximal ledge 650, a narrowed region 652, and a distal tapered region 654. The narrowed region 652 may be designed to fit within the deployment sheath 616 (e.g., a distal stent covering region of the deployment sheath 616) and the ledge 650 may abut the distal end 648 of deployment sheath 616, as shown in FIG. 16. FIG. 17 illustrates a system 710, which may be similar in form and function to other systems disclosed herein, including a deployment sheath 716 and an inner shaft 724. The distal tip 726 may be coupled to the inner shaft 724. The distal tip 726 may have a smooth transition in diameter rather than a ledge (e.g., a ledge 650 as shown in FIGS. 15-16). In addition, the distal end of the deployment sheath 716 may have a chamfered or otherwise rounded tip. Other tip geometries and profiles are contemplated.

The materials that can be used for the various components of the system disclosed herein and the various tubular members disclosed herein may include those commonly associated with medical devices. For simplicity purposes, the following discussion makes reference to the deployment sheath 16 and other components of the system 10. However, this is not intended to limit the devices and methods described herein, as the discussion may be applied to other similar tubular members and/or components of tubular members or devices disclosed herein.

The deployment sheath 16 and/or other components of the system 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer, CRISTAMID® available from Elf Atochem, VESTAMID®, or the like), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the system 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system 10 to achieve the same result.

In some embodiments, a degree of Magnetic Resonance Imaging (MM) compatibility is imparted into the system 10. For example, the system 10, or portions thereof, may be made of a material that does not substantially distort the image and create substantial artifacts (e.g., gaps in the image). Certain ferromagnetic materials, for example, may not be suitable because they may create artifacts in an Mill image. The system 10, or portions thereof, may also be made from a material that the Mill machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

U.S. Pat. No. 9,084,692 is herein incorporated by reference.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A medical device, comprising:
    an inner shaft having a stent receiving region;
    a bumper shaft disposed about the inner shaft;
    wherein the bumper shaft has a body section and a distal section with an outer diameter that is smaller than an outer diameter of the body section; and
    a deployment sheath slidably disposed about the inner shaft, the deployment sheath having a handle coupled thereto, a body region designed to be disposed within a patient during use and a distal stent covering region designed to cover the stent receiving region, the distal stent covering region having a substantially constant outer diameter that is smaller than all other portions of the deployment sheath,
    wherein the body region extends from the handle to a position adjacent to the distal stent covering region,
    wherein a first transition is disposed between the body region and the distal stent covering region of the deployment sheath, wherein a second transition is disposed between the body section and the distal section of the bumper shaft, wherein a stent having a stent length is disposed along the inner shaft, and wherein the first transition and the second transition are separated by a distance when the deployment sheath is extended distally over the stent.

2. The medical device of claim 1, further comprising a stent disposed along the stent receiving region.

3. The medical device of claim 1, wherein the distance is at least as long as the stent length.

4. The medical device of claim 1, wherein the distance is at least 1.25 times the stent length.

5. The medical device of claim 1, wherein the distance is at least 1.5 times the stent length.

6. The medical device of claim 1, further comprising a bumper positioned adjacent to the bumper shaft, the bumper having an outer diameter that is greater than an outer diameter of the bumper shaft.

7. The medical device of claim 1, wherein the distal stent covering region has a length designed to extend between a knee and an ankle of a patient.

8. The medical device of claim 1, further comprising an outer shaft disposed along at least a portion of the deployment sheath.

9. The medical device of claim 1, wherein the first transition is a step transition region.

10. The medical device of claim 1, wherein the first transition is an angled transition region.

11. A method for manufacturing a stent delivery system, the method comprising:
    disposing a bumper shaft about an inner shaft, the inner shaft having a stent receiving region;
    disposing a deployment sheath about the inner shaft, the deployment sheath having a handle coupled to a proximal end region of the deployment sheath, a body region extending from the proximal end region, a first transition region extending from the body region, and a distal stent covering region extending from the first transition region,
    the distal stent covering region having a substantially constant outer diameter that is smaller than an outer diameter of the proximal end region and smaller than an outer diameter of the body region;
    wherein the first transition region transitions in outer diameter from the outer diameter of the body region to the substantially constant outer diameter of the distal stent covering region;
    disposing a stent along the stent receiving region, the stent having a stent length;
    wherein the bumper shaft has a body portion, a distal portion, and a second transition between the body portion and the distal portion; and
    wherein the first transition is spaced from the second transition by a distance that has a length that is at least as long as the stent length.

12. The method of claim 11, wherein the distance is at least 1.25 times the stent length.

13. The method of claim 11, wherein the distance is at least 1.5 times the stent length.

14. A medical device system, comprising:
    an inner shaft having a stent receiving region;
    a self-expanding stent disposed along the stent receiving region, the stent having a stent length;
    a bumper shaft disposed about the inner shaft;
    a deployment sheath slidably disposed about the inner shaft, the deployment sheath having a handle coupled thereto, a body region extending from the handle, a first transition region extending from the body region, and a distal stent covering region extending from the first transition region, the distal stent covering region having an outer diameter that is smaller than an outer diameter of all other portions of the deployment sheath;

wherein the bumper shaft has a body portion, a distal portion, and a second transition between the body portion and the distal portion;

wherein the distal portion of the bumper shaft has an outer diameter that is smaller than an outer diameter of the body region of the bumper shaft; and wherein the first transition is spaced from the second transition by a distance that has a length that is at least as long as the stent length.

15. The medical device system of claim 14, wherein the distance is at least 1.25 times the stent length.

16. The medical device system of claim 14, wherein the distance is at least 1.5 times the stent length.

17. The medical device system of claim 14, further comprising an outer shaft disposed along at least a portion of the deployment sheath.

18. The medical device system of claim 14, wherein the first transition, the second transition, or both include an angled transition.

* * * * *